US011699514B2

(12) United States Patent
Kozloski et al.

(10) Patent No.: US 11,699,514 B2
(45) Date of Patent: Jul. 11, 2023

(54) PREDICTIVE DUAL MACHINE TRANSLATION

(71) Applicant: International Business Machines Corporation, Armonk, NY (US)

(72) Inventors: James R. Kozloski, New Fairfield, CT (US); Viatcheslav Gurev, Bedford Hills, NY (US); Jaimit Parikh, Danbury, CT (US); Paolo Di Achille, White Plains, NY (US); Zachary Shahn, Brooklyn, NY (US); Daby Sow, Croton on Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 446 days.

(21) Appl. No.: 16/885,219

(22) Filed: May 27, 2020

(65) Prior Publication Data
US 2021/0374599 A1 Dec. 2, 2021

(51) Int. Cl.
*G16H 30/40* (2018.01)
*G06N 20/00* (2019.01)
(Continued)

(52) U.S. Cl.
CPC ......... *G16H 30/40* (2018.01); *G06F 18/2133* (2023.01); *G06N 20/00* (2019.01);
(Continued)

(58) Field of Classification Search
CPC ........ G06N 20/00; G06N 3/084; G16H 10/60; G16H 50/30; G16H 30/40; G06K 9/6239
See application file for complete search history.

(56) References Cited

U.S. PATENT DOCUMENTS

2015/0012466 A1* 1/2015 Sapiro ................. G16H 50/20
706/12
2015/0293987 A1 10/2015 Andreu et al.
(Continued)

FOREIGN PATENT DOCUMENTS

KR 101898575 B1 9/2018

OTHER PUBLICATIONS

Bibb Allen, A Road Map for Translational Research on Artificial Intelligence in Medical Imaging: From the 2018 National Institutes of Health/RSNA/ACR/The Academy Workshop, Journal of the American College of Radiology, vol. 16, Issue 9, Part A, 2019, pp. 1179-1189. (Year: 2019).*

(Continued)

*Primary Examiner* — Fonya M Long
*Assistant Examiner* — Anthony Balaj
(74) *Attorney, Agent, or Firm* — Kristofer Haggerty; Otterstedt & Kammer PLLC

(57) ABSTRACT

Dual machine translators are trained by generating a translated medical image by operation of an illustrative model on an original medical record, generating information based on whether the translated medical image is natural in a modality of medical imaging, producing a back-translated medical record by operation of an interpretive model on the translated medical image, calculating a reward by comparing the back-translated medical record to the original medical record, updating parameters of the illustrative model in response to the information and the reward, and updating parameters of the interpretive model in response to the reward.

5 Claims, 10 Drawing Sheets

(51) Int. Cl.
- *G16H 50/30* (2018.01)
- *G16H 10/60* (2018.01)
- *G06F 18/2133* (2023.01)
- *G06N 3/084* (2023.01)
- *G06V 10/82* (2022.01)

(52) U.S. Cl.
CPC ............ *G16H 10/60* (2018.01); *G16H 50/30* (2018.01); *G06N 3/084* (2013.01); *G06V 10/82* (2022.01)

(56) References Cited

U.S. PATENT DOCUMENTS

| | | |
|---|---|---|
| 2016/0210749 A1 | 7/2016 | Nguyen et al. |
| 2018/0225823 A1 | 8/2018 | Zhou et al. |
| 2020/0160980 A1* | 5/2020 | Lyman ................. G06K 9/6278 |
| 2021/0007606 A1* | 1/2021 | Su ....................... A61B 5/7278 |

OTHER PUBLICATIONS

Xia, Y., Tan, X., Tian, F., Qin, T., Yu, N., & Liu, T. Y. Model-level dual learning, International Conference on Machine Learning, (Jul. 2018), (pp. 5383-5392). PMLR. (Year: 2018).*

Chartsias et al., Adversarial Image Synthesis for Unpaired Multimodal Cardiac Data, In: Tsaftaris S., Gooya A., Frangi A., Prince J. (eds) Simulation and Synthesis in Medical Imaging. SASHIMI 2017. Lecture Notes in Computer Science, vol. 10557. Springer, Sep. 2017, pp. 1-11.

Duchateau et al., Model-Based Generation of Large Databases of Cardiac Images: Synthesis of Pathological Cine MR Sequences from Real Healthy Cases, in IEEE Transactions on Medical Imaging, vol. 37, No. 3, Mar. 2018, pp. 755-766.

Lao et al., Leveraging Disease Progression Learning for Medical Image Recognition, (Submitted on Jun. 26, 2018 (v1), last revised Sep. 1, 2018 (this version, v2)), pp. 1-6.

Yi et al., "Generative Adversarial Network in Medical Imaging: A Review." Journal of Latlex Class Files, vol. 14 No 8, Aug. 2015, pp. 1-20.

Prakosa et al., Generation of Synthetic but Visually Realistic Time Series of Cardiac Images Combining a Biophysical Model and Clinical Images, in IEEE Transactions on Medical Imaging, vol. 32, No. 1, pp. 99-109, Jan. 2013.

Jing et al., On the Automatic Generation of Medical Imaging Reports, Conference paper Jan. 2018, pp. 1-10.

Alessandrini et al., A Pipeline for the Generation of Realistic 3D Synthetic Echocardiographic Sequences: Methodology and Open-Access Database, in IEEE Transactions on Medical Imaging, vol. 34, No. 7, pp. 1436-1451, Jul. 2015.

He et al., Dual learning for machine translation, In Advances in Neural Information Processing Systems, pp. 820-828, Nov. 2016.

* cited by examiner

US 11,699,514 B2

PREDICTIVE DUAL MACHINE TRANSLATION

BACKGROUND

The present invention relates to the electrical, electronic, and computer arts, and more specifically, to dual machine translators.

Increasingly, artificial intelligence (AI) is used in medical practice to support physicians' diagnoses and prognoses of physiologic conditions as well as treatment decisions. For example, in cardiology, data driven AI (e.g., deep learning) has been used for providing diagnostic, prognostic, and therapeutic indications for detection and optimal treatment of cardiac disease based on collections of longitudinal medical records.

Other forms of computation also have proven useful in medical practice. As another example, again in cardiology, biophysical modeling has produced anatomically accurate mechanistic representations of cardiac function based on medical imaging.

SUMMARY

Principles of the invention provide techniques for predictive dual machine translation between written medical history and medical imagery. In one aspect, an exemplary method includes generating a translated medical image by operation of an illustrative model on an original medical record, generating information based on whether the translated medical image is natural in a modality of medical imaging, producing a back-translated medical record by operation of an interpretive model on the translated medical image, calculating a reward by comparing the back-translated medical record to the original medical record, updating parameters of the illustrative model in response to the information and the reward, and updating parameters of the interpretive model in response to the reward.

One or more embodiments of the invention or elements thereof can be implemented in the form of a computer program product including a computer readable storage medium with computer usable program code for facilitating the method steps indicated. Furthermore, one or more embodiments of the invention or elements thereof can be implemented in the form of a system (or apparatus) including a memory that embodies computer executable instructions, and at least one processor that is coupled to the memory and operative by the instructions to facilitate exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

In view of the foregoing, techniques of the present invention can provide substantial beneficial technical effects. For example, one or more embodiments provide one or more of:

Prognostic, illustrative, coherent, virtual medical imagery based solely on textual medical records; and Prognostic, illustrative, coherent, virtual textual medical records based solely on medical imagery.

One advantage of an illustrative medical image and/or textual medical record, generated from the alternative "ground truth" medium, is to provide context for interpretation of the ground truth medium, and especially interpretation that is based on so called "black box" statistical models. For example, a set of patient states inferred from ground truth medical records, and transition probabilities inferred from these states based on sequential ground truth medical records, may be difficult to interpret if parameters of the model derive from a deep neural network. A practitioner may find it useful to peruse a coherent illustration of the likely medical image associated with these medical records in order to project these hidden, uninterpretable parameters, into a space that is recognizable and interpretable by the clinician. Even if this projection is not used to create or validate the patient states, the illustrations provided by the current invention can be helpful in providing insights into the likely correlates of the patient state in the familiar domain of medical imaging.

These and other features and advantages of the present invention will become apparent from the following detailed description of illustrative embodiments thereof, which is to be read in connection with the accompanying drawings.

DETAILED DESCRIPTION

Figure 1:
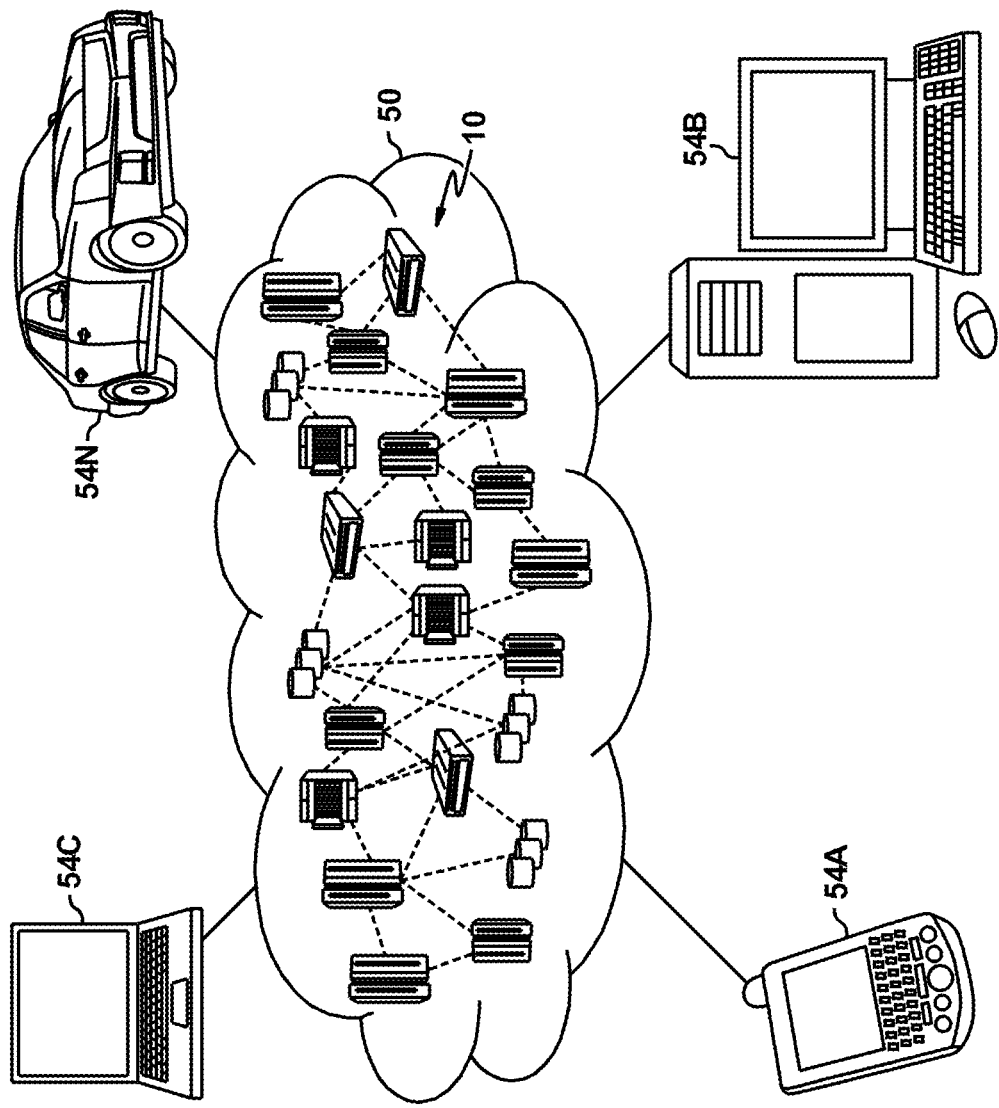
FIG. 1 depicts a cloud computing environment according to an embodiment of the present invention.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
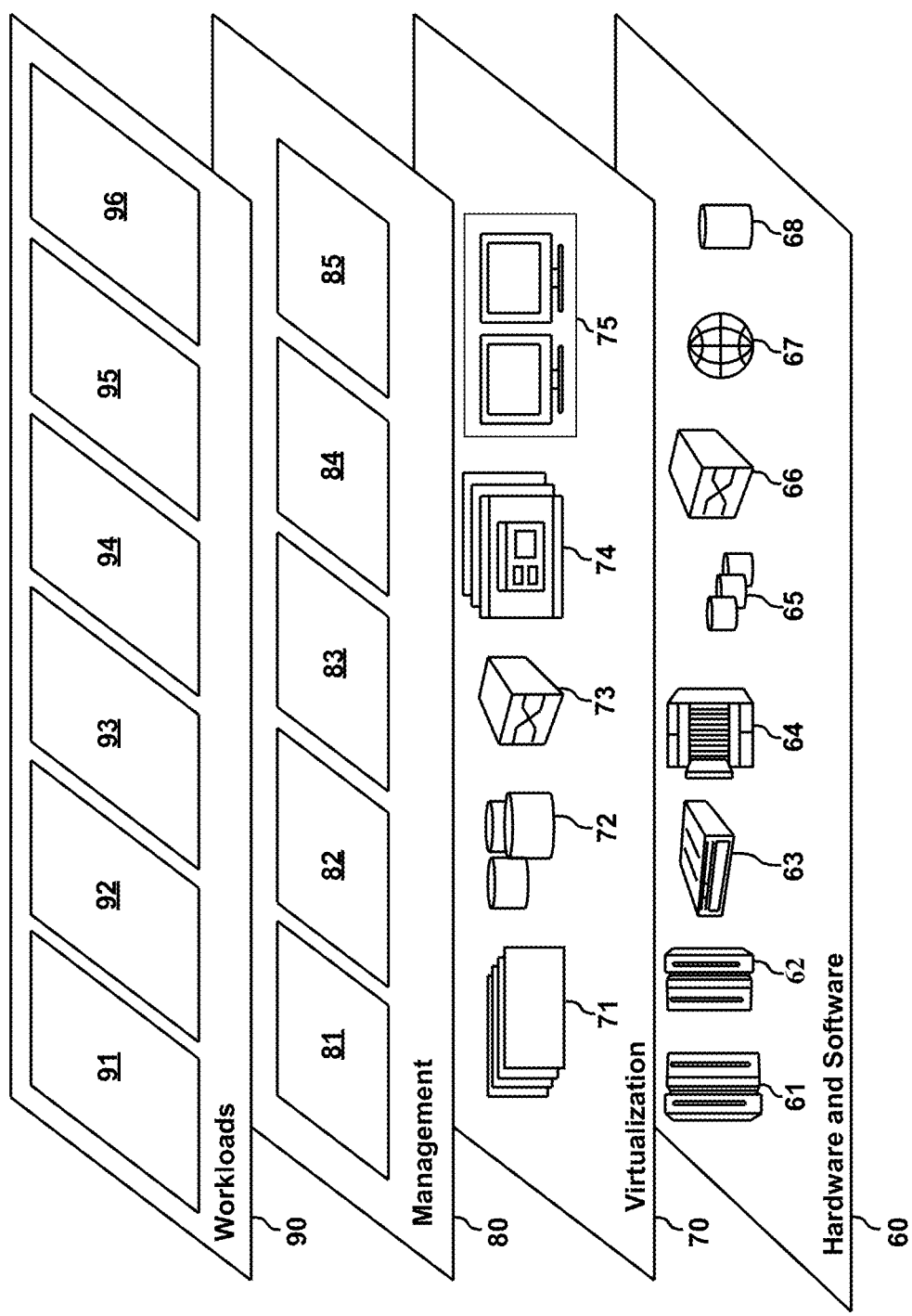
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a dual translation module 96.

Figure 3A:
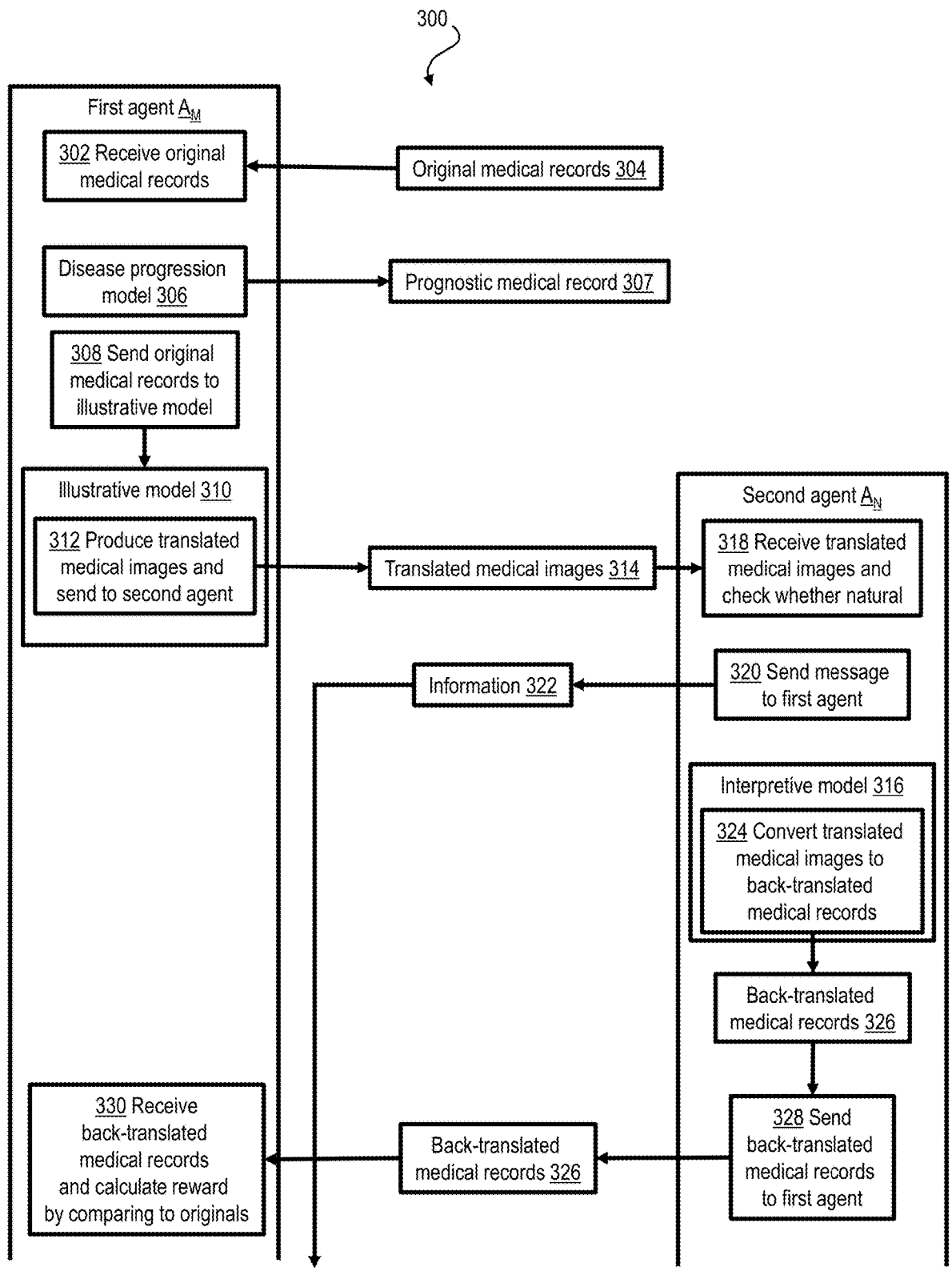
FIGS. 3A-3B depict in a flowchart a method that is implemented by a dual translation module according to an exemplary embodiment.
Figure 3B:
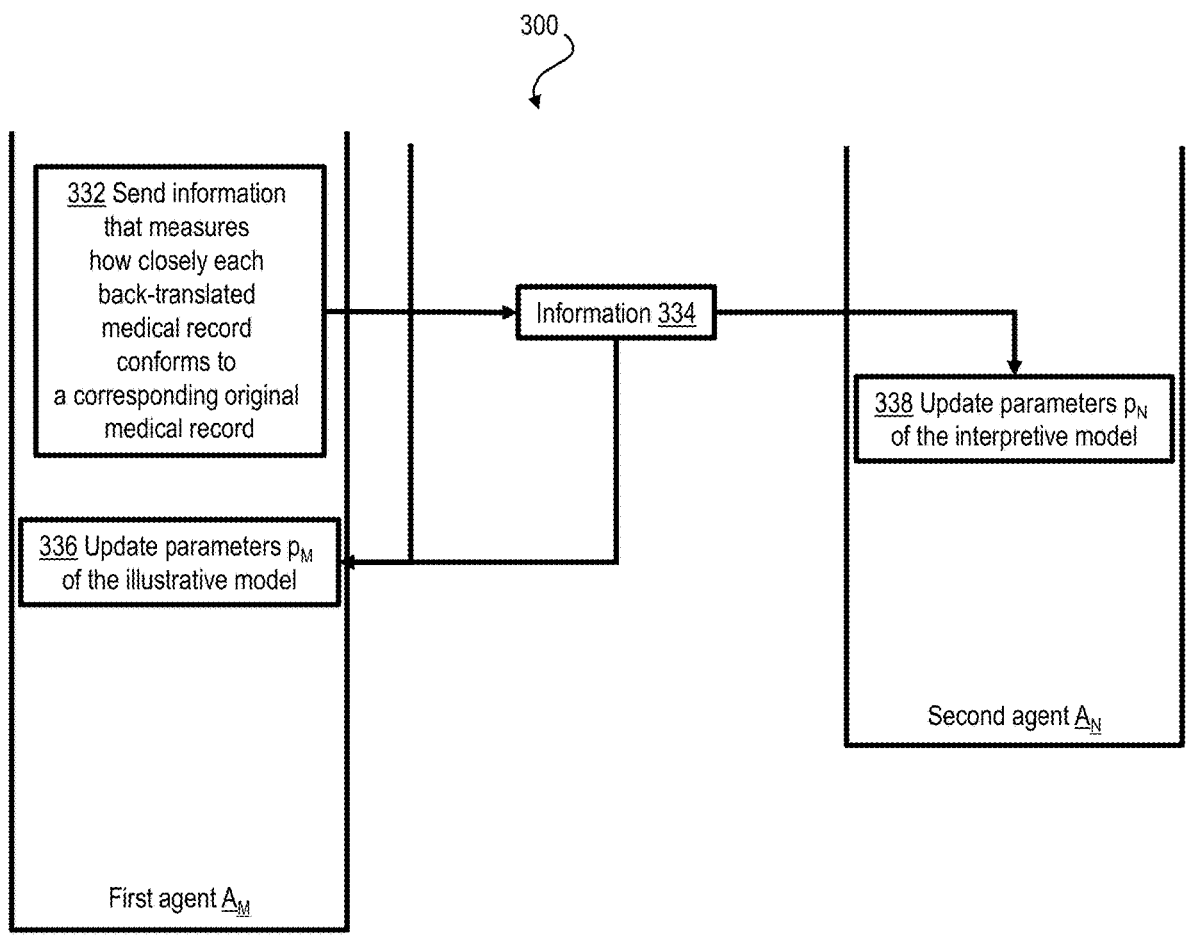
Figure 4:
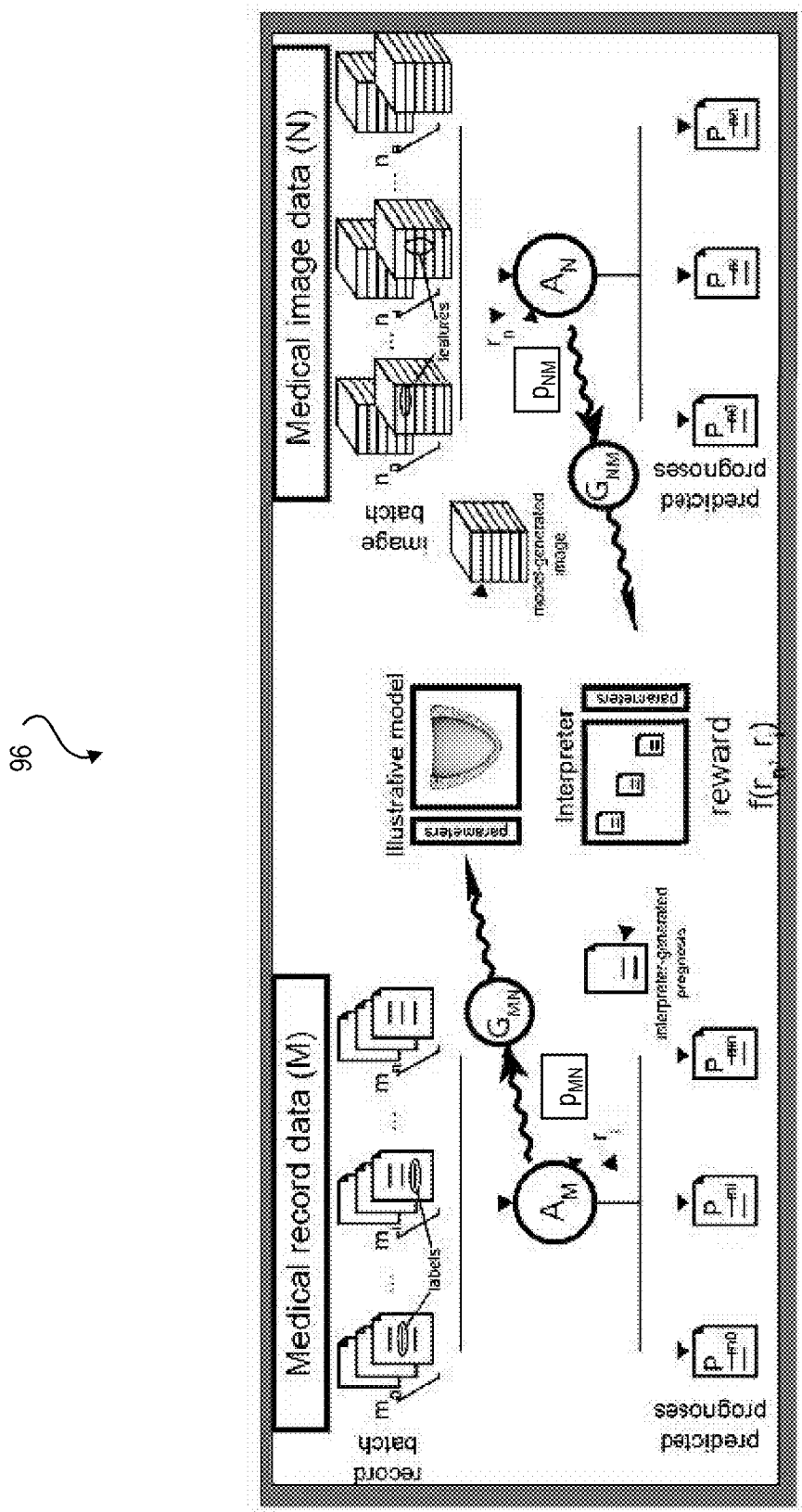
FIG. 4 depicts in a schematic components of a dual translation module according to an exemplary embodiment.

FIGS. 3A-3B depict in a flowchart a method 300 that is implemented by the dual translation module 96 according to an exemplary embodiment. FIG. 4 depicts components of the dual translation module 96 that implement the method 300. At 302, a first agent $A_M$ of the dual translation module 96 (shown in FIG. 4) receives a sequence of original medical records 304 (m in FIG. 4) in a modality M. The first agent $A_M$ includes a disease progression model (DPM) 306 (see also FIGS. 6-7). The DPM 306 is trained to produce prognoses based on labels found in the original medical records 304. For example, a heart disease progression model acting as part of $A_M$ produces a prognostic medical record 307 ($p_m$ in FIG. 4) from the sequence of original medical records 304. A parameters-generating model, $p_{MN}$, provides a second output vector from $A_M$, which is used to parameterize a Generative Pathophysiological Model (GPM or "illustrative model") 310 (GMN in FIG. 4; see also FIGS. 6-7). At 308, the first agent $A_M$ sends one or more of the original medical records 304 to the GPM 310, which also is included in the first agent $A_M$. At 312, the GPM 310 produces a sequence of one or more translated medical images based on the one or more original medical records 304, and sends the translated medical images 314 to a second agent $A_N$. Translation from the original medical records 304 to the medical images at 312 is accomplished by parameterizing and running the illustrative model 310 based on labels, categories, and features found in the original medical records 304 by the disease progression model 306 during the course of its formulating the prognostic medical record 307, then rendering the illustrative model's 310 outputs as a medical image. The problem of running the illustrative model is that of selecting, by means of the current invention, parameters of the mechanistic model consistent with the medical record labels, categories, and features, as ascertained by the disease progression model 306 and trained by the invention.

Generally, mechanistic models, such as heart models, brain circuit models, models of insulin generation in response to blood sugar, etc., can sample from the space of patient observations encountered via medical imaging modalities (e.g., echocardiography, electroencephalography, blood sugar insulin pump recordings). This sampling is evident since the models are considered useful based on their ability to access as many different categories of patient images as possible, by means of choosing different parameters of the model, such that outputs of the model match some recorded medical image of a patient. In the current art, these parameters are chosen by hand, or by means of some automatic tuning algorithm or parameter optimization scheme such as for example, genetic algorithms.

In one or more embodiments of the current invention, the parameters are chosen by means of the illustrative model receiving medical record labels, categories, or features. Choosing the parameters may be performed by any universal function approximation method, such as regression, through neural networks such as autoencoders, or by means of a look-up-table. Regression may involve setting parameters using a linear model that takes as inputs a feature vector extracted from the medical record (constructed for example using partial least square regression). As described below, an autoencoder may be trained to project medical record features into a latent space that includes the mechanistic model parameters, which after producing mechanistic model outputs, may be decoded back into the medical record features. A look-up-table may be used to take a patient category code (e.g., multiple sclerosis, in remission) and use it to look up a parameterization of a mechanistic model appropriate for that category.

The second agent $A_N$ includes a Generative Interpreter Model (GIM or "interpreter") 316 ($G_{NM}$ in FIG. 4) that is trained to produce prognoses based on labels found in medical images of a certain modality N (e.g., echocardiogram, electrocardiogram). At 318, the second agent $A_N$ receives the translated medical image(s) 314 and checks whether each image is a valid or natural image in the modality N. At 320, the second agent $A_N$ sends a message to the first agent $A_M$ with information 322 whether each of the translated medical images 314 is natural. At 324, the GIM 316 (see FIG. 5) converts each of the translated medical images 314 to a back-translated medical record 326. The GPM 310 and the GIM 316 essentially form an autoencoder, in which the latent space includes parameters of the GPM, encoded from the features of the DPM, and decoded by the GIM. The conversion of translated medical images is accomplished by the GIM 316 running its decoder portion of the autoencoder on each translated medical image 314 to produce a corresponding back-translated medical record 326 ($p_n$ in FIG. 4). The current invention provides also for utilizing a model surrogate of the GPM, such as a neural network trained to provide model outputs (samples from the space of patient imaging data) given a GPM parameter vector. In this way, having trained the model surrogate, methods for performing gradient descent (such as backpropagation) may be employed that exploit this network that has already learned the distributional mapping from GPM parameter space to the space of patient measures. In this way the autoencoder may be trained by means of backpropagation based on loss measured at the back-translated medical record through the generated medical image, and continuing to the encoder, which is responsible for selecting parameters from the prior distribution of parameters in order to create a coherent medical image sample. Note that the back-translated medical records 326, in one or more embodiments, may extend beyond the prognoses output by the DPM 306 because the GIM 316 is tasked with modeling medical record data that the DPM 306 was not originally trained to model. At 328, the second agent $A_N$ sends the back-translated medical records 326 to the first agent $A_M$. For example, an echocardiogram reading model acting as $A_N$ produces a prognosis from N. A parameters-generating model, $p_{NM}$, provides a second output vector from $A_N$, which is used to parameterize the GIM 316. The medical record generator (GIM or interpreter 316) produces a complete medical record for the patient ($p_n$ in FIG. 4), which is then provided to the first disease progression model agent, $A_M$, for further analysis.

At 330, the first agent $A_M$ receives the back-translated medical records 326 and compares them to the original medical records 304. At 332, the first agent $A_M$ sends to the second agent $A_N$ information or a reward 334 ($f(r_n, r_i)$ in FIG. 4) that measures how closely each of the records 326 conforms to a corresponding one of the original medical records 304. In one or more embodiments, the information 334 can be in the nature of error differentials. For example, the heart disease progression model checks the record it receives from the medical record generator and compares it to an original patient record.

At 336, the first agent $A_M$ updates parameters $p_M$ of the GPM 310 in response to the information 322, 334. For example, in case the information 322 indicates that the translated medical images 314 were natural, that information reinforces the existing parameters $p_M$; on the other hand, in case the translated medical images 314 were not natural, that information prompts changes to the parameters $p_M$ in a manner that will be apparent to one having ordinary skill in the art of AI and generative classifiers. At 338, the second agent $A_N$ updates parameters $p_N$ of the GIM 316 in response to the information 334. For example, in case the reward 334 indicates that the back-translated medical records 326 match the original medical records 304, that information reinforces the existing parameters $p_M$, $p_N$; on the other hand, in case the reward 334 is small or negative (indicates the back-translated medical records 326 do not match the original medical records 304), that information prompts changes to the parameters $p_M$, $p_N$. One of ordinary skill in the art would understand that, in one or more embodiments, reinforcement learning uses rewards associated with updates or transitions. Reinforcement learning is an area of machine learning concerned with how software agents take actions (e.g., updates or transitions) in an environment in order to maximize a notion of cumulative reward. Stated simply, reinforcement learning is a machine learning paradigm.

Reinforcement learning techniques do not require labeled input/output pairs, and do not require sub-optimal actions to be explicitly corrected. Instead reinforcement learning techniques attempt to find a balance between exploration (of uncharted territory) and exploitation (of current knowledge). The environment of the algorithm can be stated in the form of a Markov decision process (MDP) and may utilize dynamic programming techniques. Moreover, reinforcement learning techniques need not assume knowledge of an exact mathematical model of the MDP and they can be useful for large MDPs where exact methods become infeasible.

In one or more embodiments, the method 300 can be repeated until the parameters $p_M$ and $p_N$ converge, e.g., until at each iteration of the method 300 the parameters $p_M$, $p_N$ change by no more than 3 percent. In one or more other embodiments, the method 300 can be repeated until the information 322, 334 (which generally can be in the nature of error differentials) is less than a threshold value. After training on anonymized actual patient data, when the parameters have converged, the GPM 310 becomes a useful Illustrative Artificial Intelligence (IAI) that can show a heart model to a cardiologist (or some other sort of medical image to some other sort of specialist) based only on the text of a patient medical record; while the GIM 316 becomes a useful diagnostic tool that can generate text for a patient's medical record based only on a medical image.

Thus, referring to FIG. 4, the dual translation module 96 comprises a records-based disease progression model $A_M$ that operates on medical records to predict a subsequent patient state and medical record, and an images-based disease progression model $A_N$ that operates on medical images to predict a subsequent patient state and medical image. The dual translation module 96 also comprises a generative model GMN that produces a pathophysiological simulation (medical images sequence) of a patient given a sequence of medical records, and a generative model $G_{NM}$ that produces a sequence of medical records based on an interpretation of a medical image and simulation of a patient state. The disease progression model $A_M$ is trained by, for example, assuming that features under each patient state follow independent Gaussian distributions. Note that these states are not directly observed. The goal in this approach is to estimate parameters of the progression model and states of the progression model simultaneously. The Expectation-Maximization (EM) algorithm is then used to estimate the parameters. In one or more embodiments, the disease progression model $A_N$ is trained by using a generative adversarial approach. Specifically, a GAN latent feature space may be used to create an accurate subject specific forecast for a typical image progression by reducing the subject's magnetic resonance (MR) image to a latent feature space and adding the isolated latent features, before reconstructing the image from the new latent encoding.

In one or more embodiments, the GPM 310 and the GIM 316 are trained by a dual-learning algorithm in which a parameter generating model and an interpreter reward are combined for a total system reward. This scheme avoids the need for a dual corpus, since the combination of these two rewards are intended to verify only: 1) the GPM can produce sequences of medical images from medical records which are consistent with the parameters of the generative imaging progression model $A_N$ (e.g., not gibberish) and 2) the GPM can produce sequences of medical images sufficient in information content to recover the original medical record sequence. In one or more embodiments, the dual translation module 96 implements an IAI that produces a sequence of medical images from a medical record of symptoms; the sequence of medical images demonstrate likely pathophysiology and dynamics responsible for a forecast of patient symptom progression.

Figure 5:
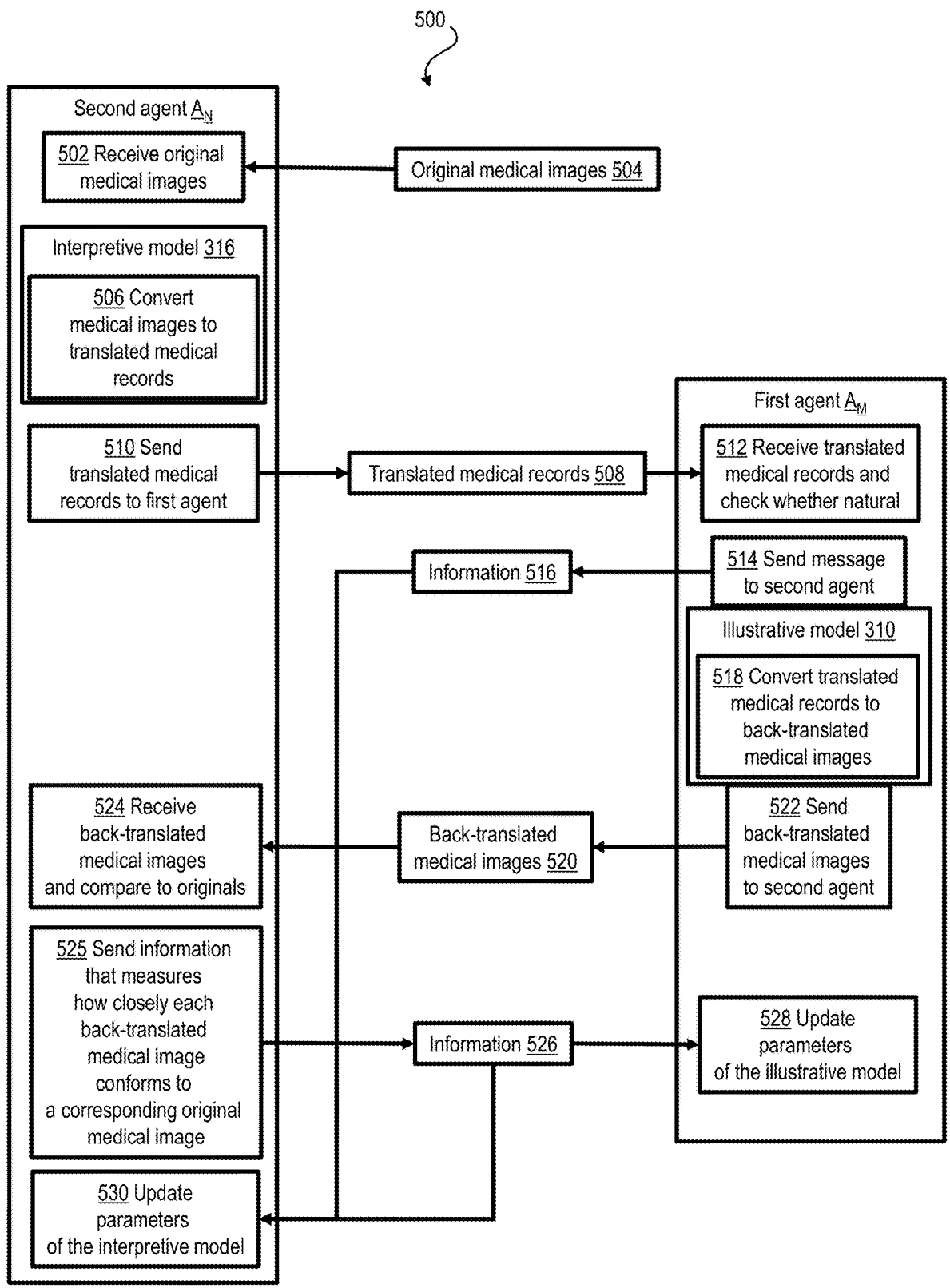
FIG. 5 depicts in a flowchart another method that is implemented by the dual translation module according to an exemplary embodiment.

FIG. 5 depicts in a flowchart another method 500 that is implemented by the dual translation module 96 according to some embodiments. At 502, the second agent $A_N$ of the dual translation module 96 receives a sequence of original medical images 504 in the modality N. At 506, the GIM 316 of the second agent $A_N$ converts each of the original medical images 504 to a translated medical record 508 in the modality M. At 510, the second agent $A_N$ sends the translated medical records 508 to the first agent $A_M$.

At 512, the first agent $A_M$ receives the translated medical records 508 and checks whether each record is valid or natural within the modality M. At 514, the first agent $A_M$ sends a message to the second agent $A_N$ with information 516 whether each of the translated medical records 508 is natural. At 518, the GPM 310 converts each of the translated medical records 508 to a back-translated medical image 520.

At 522, the first agent $A_M$ sends the back-translated medical images 520 to the second agent $A_N$.

At 524, the second agent $A_N$ receives the back-translated medical images 520, compares them to the original medical images 504. At 525, the second agent sends to the first agent $A_M$ information 526 that measures how closely each of the images 520 conforms to a corresponding original medical image 504. In one or more embodiments, the information 526 can be in the nature of error differentials.

At 528, the first agent $A_M$ updates parameters $p_M$ of the GPM 310 in response to the information 526. At 530, the second agent $A_N$ updates parameters $p_N$ of the GIM 316 in response to the information 516, 526.

Figure 6:
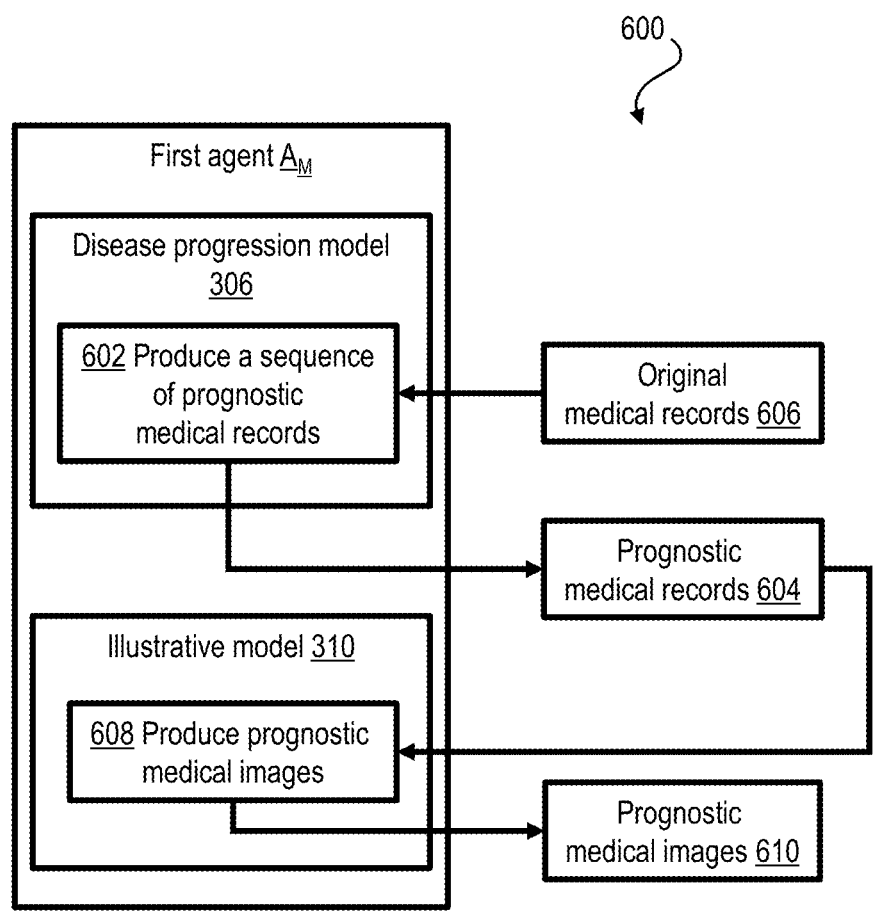
FIG. 6 depicts in a flowchart another method that is implemented by the dual translation module according to an exemplary embodiment.
Figure 7:
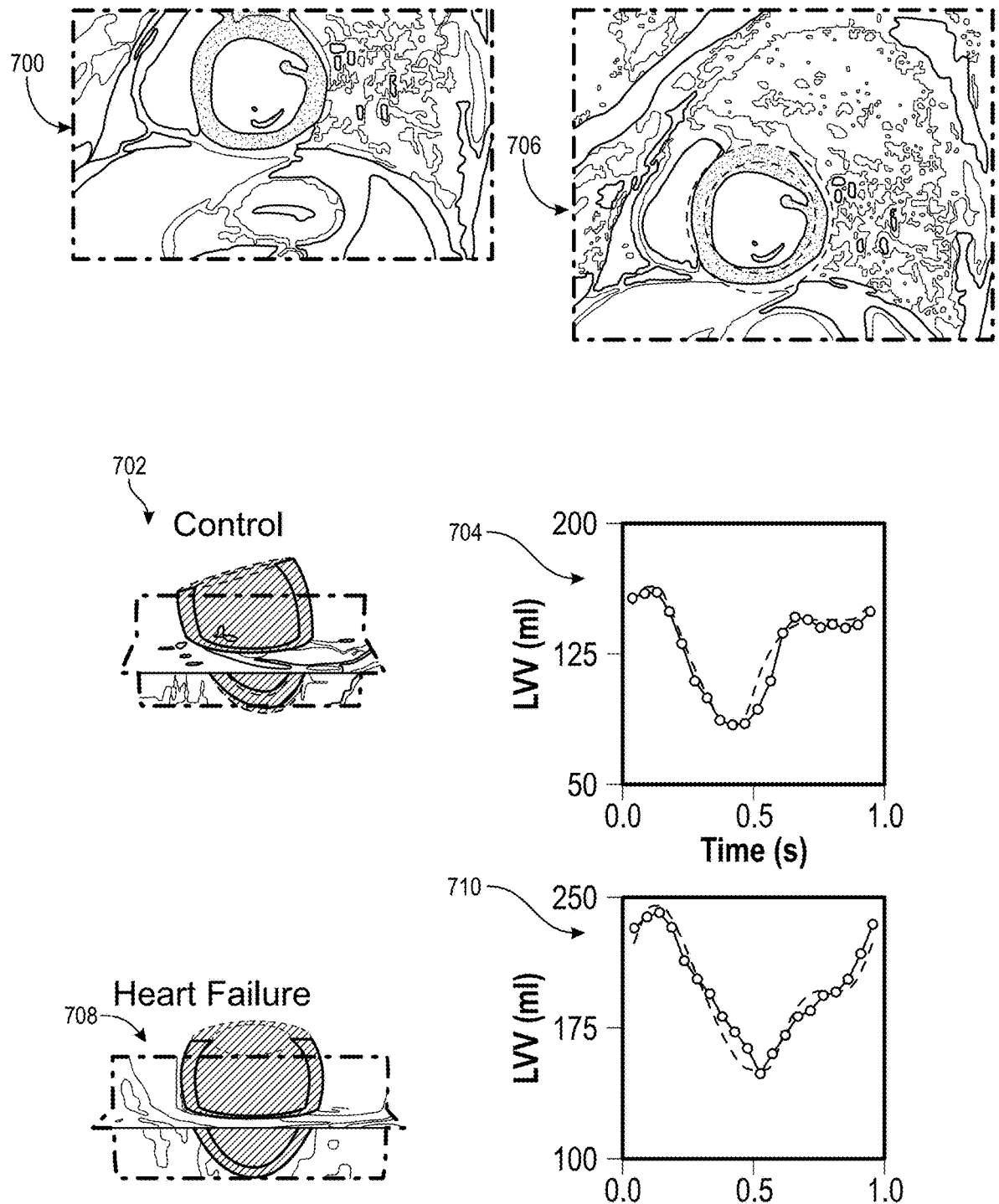
FIG. 7 depicts medical images (sonograms) of a normal heart and of a failing heart.

FIG. 6 depicts in a flowchart another method 600 that is implemented by the dual translation module 96 according to an exemplary embodiment. At 602, the DPM 306 produces a sequence of prognostic medical records 604 from a sequence of original medical records 606. At 608, the trained GPM 310 produces a sequence of prognostic medical images 610 based on the prognostic medical records 604. FIG. 7 shows exemplary GPM output (e.g., prognostic medical images 610). The images correspond to heart geometries and contraction profiles consistent with the patient state. Image 700 shows a magnetic resonance image (MRI) of a control (normal) heart contraction, together with an automated image segmentation (speckled torus) providing left ventricular (LV) boundaries for each patient. An idealized 6-parameter model of LV geometry was fitted to the segmentation results to obtain geometric parameters of a cardiac model based on image analysis. Image 702, generated on the basis of the 6-parameter model, shows a discretization of the computational domains considered as representative of a normal control left ventricle, extracted from the Sunnybrook Cardiac MRI database. Image 702 shows a cross-sectional profile matching end-diastolic configuration overlaid with corresponding MRI slices of the control heart. Image 704 shows simulated left ventricular volume (LVV) over time for the control heart and the corresponding trace extracted from MRI images. On the other hand, image 706 shows an MRI of a failing heart contraction, and image 708 shows a discretization of the computational domains considered as representative of a left ventricle undergoing heart failure, extracted from the Sunnybrook Cardiac MRI database. Image 708 shows a cross-sectional profile matching end-diastolic configuration overlaid with corresponding MRI slices of the heart failure heart. Image 710 shows simulated left ventricular volume over time for the failing heart and the corresponding trace extracted from the MRI images.

Figure 8:
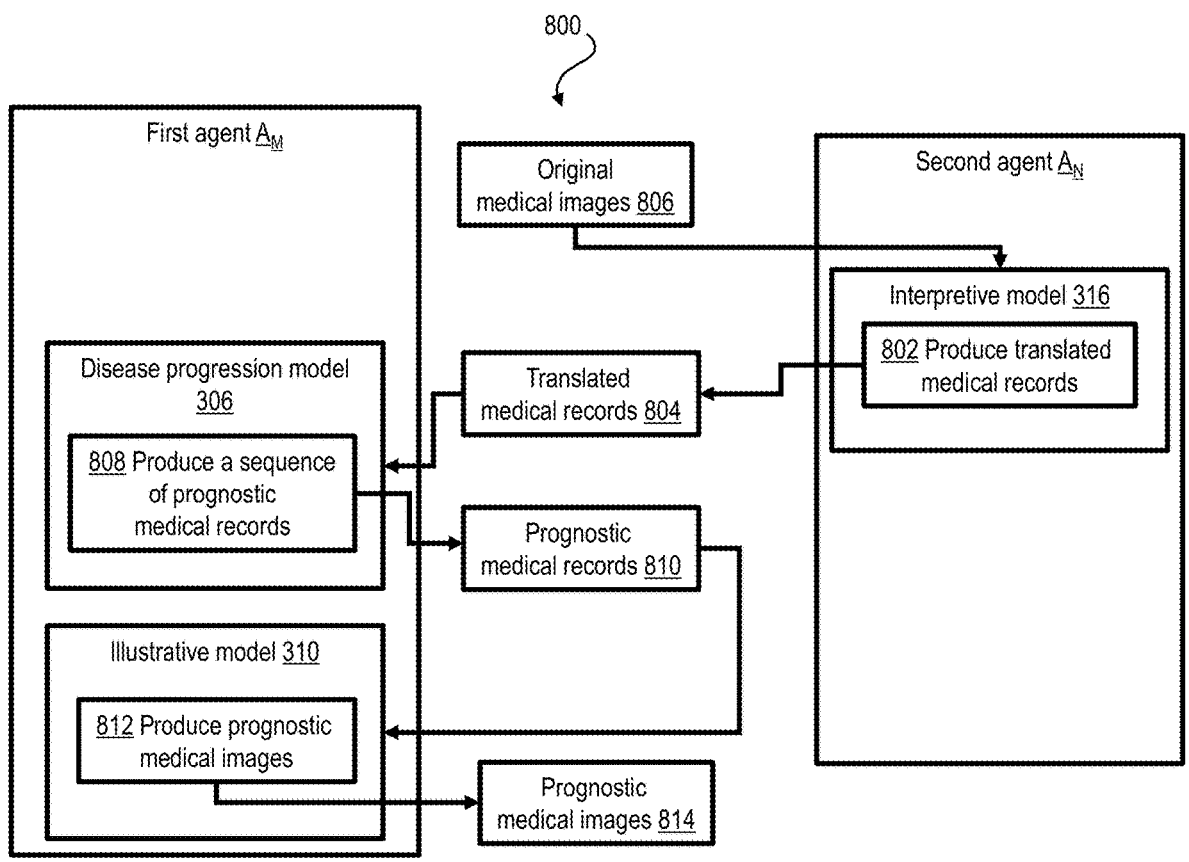
FIG. 8 depicts in a flowchart another method that is implemented by the dual translation module according to an exemplary embodiment.

FIG. 8 depicts in a flowchart another method 800 that is implemented by the dual translation module 96 according to an exemplary embodiment. At 802, the trained GIM 316 produces a sequence of translated medical records 804 from a sequence of original medical images 806. At 808, the DPM 306 produces a sequence of prognostic medical records 810 from the sequence of translated medical records 804. At 812, the GPM 310 produces a sequence of prognostic medical images 814 from the sequence of prognostic medical records 810.

Generally, a neural network includes a plurality of computer processors that are configured to work together to implement one or more machine learning algorithms. The implementation may be synchronous or asynchronous. In a neural network, the processors simulate thousands or millions of neurons, which are connected by axons and synapses. Each connection is enforcing, inhibitory, or neutral in its effect on the activation state of connected neural units. Each individual neural unit has a summation function which combines the values of all its inputs together. In some implementations, there is a threshold function or limiting function on at least some connections and/or on at least some neural units, such that the signal must surpass the limit before propagating to other neurons. A neural network can implement supervised, unsupervised, or semi-supervised machine learning.

Illustrating underlying pathophysiological causes and dynamics has been attempted in various modeling efforts using simple abstract, or costly and detailed biophysical models, but each has been executed without a formal translational aspect from medical records to simulated medical images. Purely data driven techniques using deep learning have achieved encouraging success in providing diagnostic, prognostic and therapeutic indications for the early detection and optimal treatment of cardiac disease given a collection of longitudinal medical records. Their application in the clinical practice has, however, been limited due to difficulties in interpreting how model predictions were generated. On the other hand, sophisticated numerical modeling techniques have leveraged recent advances in medical imaging to construct mechanistic representations of cardiac function that are anatomically accurate and that can reproduce well the biophysics underlying the pathophysiological state of a patient. Despite being easily interpretable, typical biophysical models do not provide indications on the likely progression of disease. Mechanistic models have therefore failed to meet clinicians' expectations for computational tools that merge multimodality data sources into interpretable kinetic models of cardiac disease progression.

The competition between mechanistic heart modeling and data driven AI for cardiology is a false one. A merger of the two is required.

Given the discussion thus far, it will be appreciated that, in general terms, an exemplary method, according to an aspect of the invention, includes at 312 generating a translated medical image 314 by operation of an illustrative model 310 on an original medical record 304; at 318 generating information 322 based on whether the translated medical image is natural in a modality of medical imaging; at 324 producing a back-translated medical record 326 by operation of an interpretive model 316 on the translated medical image; at 330 calculating a reward 334 by comparing the back-translated medical record to the original medical record; at 336 updating parameters of the illustrative model in response to the information 322 and the reward 334; and at 338 updating parameters of the interpretive model in response to the reward 334. In one or more embodiments, the method also includes training the illustrative model and the interpretive model by repeatedly generating, producing, calculating, and updating until the parameters of the illustrative model and the parameters of the interpretive model converge.

In one or more embodiments, the method also includes generating a plurality of translated medical images by operation of the trained illustrative model on a plurality of original medical records. In one or more embodiments, the method also includes at 602 producing a prognostic medical record 604 by operation of a text-based disease progression model 306 on the original medical record 606. In one or more embodiments, the method also includes at 608 producing a prognostic medical image 610 by operation of the illustrative model 310 on the prognostic medical record. In one or more embodiments, the method further comprises at 802 producing a translated medical record 804 by operation of the trained interpretive model 316 on an original medical image 806, then at 808 producing a prognostic medical record 810 by operation of a text-based disease progression model 306 on the translated medical record. In one or more embodiments, the method further comprises at 812 producing a prognostic medical image 814 by operation of the illustrative model 310 on the prognostic medical record 810.

Figure 9:
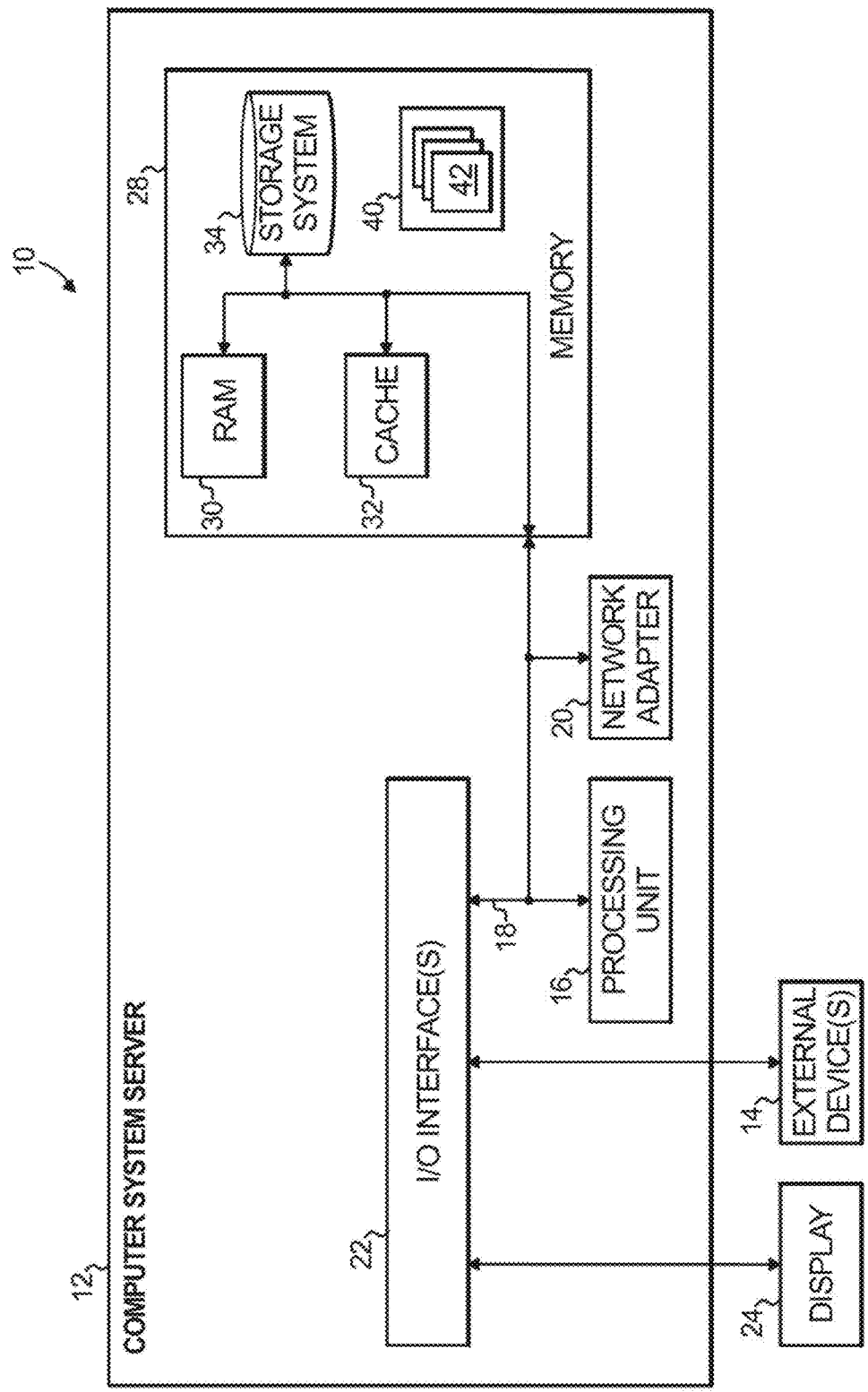
FIG. 9 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps, or in the form of a non-transitory computer readable medium embodying computer executable instructions which when executed by a computer cause the computer to perform exemplary method steps. FIG. 9 depicts a computer system that may be useful in implementing one or more aspects and/or elements of the invention, also representative of a cloud computing node according to an embodiment of the present invention. Referring now to FIG. 9, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 9, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 9) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus comprising:
    a memory embodying computer executable instructions; and
    at least one processor, coupled to the memory, and operative by the computer executable instructions to facilitate a method of:
    generating a translated medical image by operation of an illustrative model on an original medical record;
    generating information based on whether the translated medical image is natural in a modality of medical imaging;
    producing a back-translated medical record by operation of an interpretive model on the translated medical image;
    calculating a reward by comparing the back-translated medical record to the original medical record;
    updating parameters of the illustrative model in response to the information and the reward;
    updating parameters of the interpretive model in response to the reward;
    training the illustrative model and the interpretive model by repeatedly generating, producing, calculating, and updating until the parameters of the illustrative model and the parameters of the interpretive model converge; and
    generating a plurality of translated medical images by operation of the trained illustrative model on a plurality of original medical records.

2. The apparatus of claim 1 wherein the method further comprises producing a prognostic medical record by operation of a text-based disease progression model on the original medical record.

3. The apparatus of claim 2 wherein the method further comprises producing a prognostic medical image by operation of the illustrative model on the prognostic medical record.

4. An apparatus comprising:
    a memory embodying computer executable instructions; and
    at least one processor, coupled to the memory, and operative by the computer executable instructions to facilitate a method of:
    generating a translated medical image by operation of an illustrative model on an original medical record;

generating information based on whether the translated medical image is natural in a modality of medical imaging;

producing a back-translated medical record by operation of an interpretive model on the translated medical image;

calculating a reward by comparing the back-translated medical record to the original medical record;

updating parameters of the illustrative model in response to the information and the reward;

updating parameters of the interpretive model in response to the reward;

training the illustrative model and the interpretive model by repeatedly generating, producing, calculating, and updating until the parameters of the illustrative model and the parameters of the interpretive model converge; and producing a translated medical record by operation of the trained interpretive model on an original medical image, then producing a prognostic medical record by operation of a text-based disease progression model on the translated medical record.

5. An apparatus comprising:

a memory embodying computer executable instructions; and at least one processor, coupled to the memory, and operative by the computer executable instructions to facilitate a method of:

generating a translated medical image by operation of an illustrative model on an original medical record;

generating information based on whether the translated medical image is natural in a modality of medical imaging;

producing a back-translated medical record by operation of an interpretive model on the translated medical image;

calculating a reward by comparing the back-translated medical record to the original medical record;

updating parameters of the illustrative model in response to the information and the reward;

updating parameters of the interpretive model in response to the reward;

training the illustrative model and the interpretive model by repeatedly generating, producing, calculating, and updating until the parameters of the illustrative model and the parameters of the interpretive model converge; and producing a translated medical record by operation of the trained interpretive model on an original medical image, then producing a prognostic medical record by operation of a text-based disease progression model on the translated medical record.

\* \* \* \* \*